United States Patent
Hugues et al.

(10) Patent No.: US 6,235,956 B1
(45) Date of Patent: May 22, 2001

(54) ACETALS, THEIR PREPARATION AND THEIR USE

(75) Inventors: François Hugues; Alain Forestiere, both of Vernaison; Lucien Saussine, Croissy sur Seine; Dominique Commereuc, Meudon, all of (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/217,584

(22) Filed: Dec. 22, 1998

(30) Foreign Application Priority Data

Dec. 22, 1997 (FR) .................................................. 97 16455
Dec. 22, 1997 (FR) .................................................. 97 16459

(51) Int. Cl.$^7$ .............................. C07C 2/32; B01J 31/00; C07D 307/02
(52) U.S. Cl. .................... 585/511; 585/520; 502/169; 502/171; 502/172; 549/206; 549/210; 549/472; 549/502
(58) Field of Search .................................... 568/594, 591; 549/206, 210, 472, 502; 502/172, 171, 169; 585/511, 520

(56) References Cited

U.S. PATENT DOCUMENTS

| 2,490,337 | 12/1949 | Croxall et al. ............... | 260/615 |
|---|---|---|---|
| 2,691,684 | 10/1954 | Frevel et al. ................ | 260/615 |
| 5,345,023 | * 9/1994 | Chauvin et al. ............. | 585/527 |
| 5,399,778 | * 3/1995 | Steffen et al. .............. | 568/591 |
| 5,496,783 | * 3/1996 | Chauvin et al. ............. | 502/125 |
| 5,811,619 | * 9/1998 | Commereuc et al. ......... | 585/520 |

FOREIGN PATENT DOCUMENTS

| 1293143 | 4/1969 | (DE) . |
|---|---|---|
| 271091 | 6/1988 | (EP) . |
| 578541 | 1/1994 | (EP) . |
| 803489 | 10/1997 | (EP) . |
| 95/19332 | 7/1995 | (WO) . |
| 9519332 | 7/1995 | (WO) . |

OTHER PUBLICATIONS

Chemical Abstracts, vol. 57, No. 2, (1962), and Lawesson, S.O. "The Preparation of Aldehydes and Ketones from Ethers," *Ark. Kemi,* vol. 17, pp. 465–473, (1961), No month provided.

Vasickova, "Infrared Spectra of Compounds with the Methoxymethyl Protecting Group," *Collection Czechoslovak Chem. Comm.,* vol. 51, pp. 90–100, (1986), No month provided.

Barot, "Preparation of Formaldehyde, and Acetaldehyde Acetals," *Journal of Organic Chemistry,* vol. 46, No. 14, pp. 2981–2983, (1981), No month provided.

Wortel et al., "Synthesis of Acetals using Molecular Sieves III. The Use of Solid Acids as Catalysts," *Journal of the Royal Netherlands Chemical Society,* pp. 44–49 (1977), No month provided.

Roelofsen et al., "Synthesis of Acetals using Molecular Sieves," *Recueil,* vol. 90., pp. 1141–1152, (1971), No month provided.

Pernak et al., "Wirking neuer quaterar Iminiumverbindungen gegenuber Bakterienund Philzstammen," *Pharmazie,* vol. 43, pp. 654–655, (1988)

\* cited by examiner

*Primary Examiner*—Rosalynd Keys
(74) *Attorney, Agent, or Firm*—Millen, White, Zelano & Branigan, P.C.

(57) ABSTRACT

An acetal, wherein the acetal is 2,2-di(tetrahydrofurfuryloxy)propane as well as processed for producing the acetal and methods of using the acetal.

8 Claims, No Drawings

ACETALS, THEIR PREPARATION AND THEIR USE

The present invention relates to acetals, to methods for preparing them and to their use.

Within the context of research into catalysts for oligmerizing ethylene to light alpha-olefins, the Applicant became interested in acetals which can form a complex with zirconium which have high catalytic activity for this particular oligomerization reaction.

The prior art describes two general methods for synthesizing ketone acetals. One method consists of reacting an ortho-ester with a ketone to produce the desired ketone acetal. The same acetals are obtained using a second type of reaction which consists of reacting an acetylene substituted with two moles of alcohol. Other methods for synthesizing acetals can be added to those two principal methods: one method which consists of reacting an aldehyde or a ketone with one—or more—alcohols, and a method, known as transacetalization; using an acetal and an alcohol. Other indirect methods for synthesizing acetals are also known, but are seldom used.

"Non cyclic" acetals can be synthesized using conventional prior art methods. The term "non cyclic acetal" as used in the present description means acetals with the formula below in which groups R1 and R2 do not form a cycle.

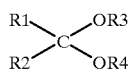

They can be synthesised using transacetalization. That synthesis thus necessitates displacing the equilibrium towards the desired acetal to obtain good yields and to separate the desired acetal from other products and excess reactants. The acetal can be separated from the other constituents of the mixture by distillation when the boiling points of the different constituents of the mixture allow it; also distillation of an alcohol-acetal azeotrope can be used if one exists. If no alcohol-acetal azeotrope exists, other means must be employed to isolate the desired acetal.

A study of the prior art reveals a number of documents on acetal synthesis.

Thus N. B. Lorette and W. L. Howard, in Organic Synthesis Coll. Vol. V, p. 5, describe a general method for synthesising acetals from acetone by transacetalization from 2,2-di(methoxy)propane and the alcohol corresponding to the desired acetal. In those syntheses, the acetals are such that groups R3 and R4 in the above general formula are identical. The term "alcohol corresponding to the desired acetal" means an alcohol with formula R3OH (or R4OH since R3 and R4 are identical).

Fieser and Fieser, in "Reagents for Organic Synthesis", Vol. 5, p. 360, describe a further method for synthesizing acetone acetals from 2-methoxypropene.

In the prior art documents, two indirect methods for synthesizing formol acetals have been retained. A first method by B. S. Bal and H. W. Pinnick in J. Org. Chem. Vol. 44, p. 3727–3728 (1979) describes producing formaldehyde acetals from the alcohol corresponding to the desired acetal dimethylsulphoxide and trimethylchlorosilane. In those syntheses, the acetals are such that groups R3 and R4 in the above general formula are identical.

A further method by B. C. Barot, H. W. Pinnick in J. Org. Chem. Vol. 46, p. 2981–2983 (1981). describes producing symmetrical formol acetals by interconversion of a disymmetrical acetal with elimination of the volatile symmetrical acetal.

The acetals of the present invention are acetone acetals and formol acetals which are represented by the following general formula:

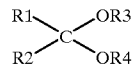

where R1 and R2 are methyl groups and R3 and R4, which are identical, are 2,2-dimethylpropyl groups, or hexyl groups, or decyl groups, or dodecyl groups, or tetradecyl groups, or hexadecyl groups, or octadecyl groups or tetrahydrofurfuryl groups;

or where R1 and R2 are methyl groups and R3 and R4 are different and are a methyl group and an octadecyl group;

or where R1 and R2 are hydrogen atoms and R3 and R4 are identical and are hexyl groups or 2-ethylhexyl groups, or hexadecyl groups.

Straight chain alcohols in particular can be used, to obtain the following compounds in which R1 and R2 are methyl groups and R3 and R4 are two n-hexyl groups, or two n-decyl groups, or two n-dodecyl groups, or two n-tetradecyl groups, or two n-hexadecyl groups, or two n-octadecyl groups or a methyl group and an n-octadecyl group; or in which R1 and R2 are hydrogen atoms and R3 and R4 are two n-hexyl groups, or two n-hexadecyl groups.

A first series of acetone acetals was synthesized by transacetalization of 2,2-di(methoxy)propane using the general procedure described by N. B. Lorette and W. L. Howard; a further disymmetrical acetal was then synthesized using the method described by Fieser and Fieser.

Further, formol acetals were synthesized using the method described by B. S. Bal and H. W. Pinnick.

The acetals of the present invention were synthesized, separated and purified using conventional purification and separation processes the selection of which depends on the specifications of each acetal. These products were characterized by their nuclear magnetic resonance spectrum using di-deuterated dichloromethane (NMR ($CD_2Cl_2$)) and in some cases by infra red (IR) spectroscopy. , These acetals were then complexed with a zirconium compound and the activity of these complexes for oligomerizing ethylene to alpha olefins was measured. This zirconium compound may be a zirconium halide and more particularly a zirconium tetrahalide such as zirconium tetrachloride $ZrCl_4$, zirconium tetraiodide $ZrI_4$, zirconium tetrabromide $ZrBr_4$, or zirconium tetrafluoride $ZrF_4$. This zirconium compound can also be a derivative with formula $ZrR'_4$ where R' is an alkoxy group with formula R"O, or an amido group with formula $R''_2N$ or a carboxylate group with formula R"COO; R" is thus a hydrocarbyl group or an alkyl group preferably containing about 1 to 30 carbon atoms. These alkoxide compounds are, for example, zirconium tetrapropylate with formula $Zr(OC_3H_7)_4$, zirconium tetrabutylate with formula $Zr(OC_4H_9)_4$; an example of the carboxylate compounds is tetra-2-ethyl-2-hexanate $Zr(OCOC_7H_{15})_4$.

The zirconium compound can also be an oxycarboxylate such as dizirconium-oxo-hexaethyl-2-hexanoate with formula $[Zr(OCOC_7H_{15})_3]_2O$.

The present invention also relates to a process more particularly for synthesizing certain acetals be reacting a non cyclic carbonyl compound such as an aldehyde or a ketone with general formula R'1R'2C=O where R'1 and R'2, which may be identical or different, are hydrogen or aryl groups or linear or branched alkyl groups containing 1 to 20 carbon atoms, limits included, with at least one alcohol with general formula R'OH where R' is a linear or branched hydrocarbon group containing 1 to 20 carbon atoms, limits included.

This particular aspect of the present invention relates to a process for synthesizing acetals from at least one alcohol R'OH in which R' is a linear or branched alkyl group containing 1 to 20 carbon atoms, limits included, preferably 4 to 16 carbon atoms, limits included. More particularly, the present invention provides a process for synthesizing acetals from at least one alcohol with formula R'OH where R' is a branched alkyl group, in particular an alkyl group containing a branch in the 2 position, such as 2-ethylhexyl.

The prior art describes two general methods for synthesizing ketone acetals. One method consists of reacting an ortho-ester with a ketone to produce the desired ketone acetal. The same acetals are obtained using a second type of reaction which consists of reacting an acetylene substituted with two moles of alcohol. Other methods for synthesizing acetals can be added to those two principal methods: one method which consists of reacting an aldehyde or a ketone with one—or more—alcohols, and a method, known as transacetalization, using an acetal and an alcohol. Other indirect methods for synthesizing acetals are also known, but are seldom used.

A study of the prior art reveals the following documents for acetal synthesis in particular.

These documents are: C. R. Hebd. Séances Acad. Sci., 257 <1963> p. 690–692, which describes the production of di-sec-octyloxy-2,2-propane, and U.S. Pat. No. 5,399,778, which describes the production of linear or branched chain ketals with general formula:

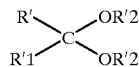

where R' and R'1 are alkyl or aryl groups containing 1 to 8 carbon atoms or R' and R'1 together with the carbon to which they are bonded-form a —(CH$_2$)$_4$— or —(CH$_2$)$_5$— cycle, and in which R'2 is a linear or branched alkyl group containing 2 to 8 carbon atoms.

The synthesis of acetals from aldehydes or ketones and alcohols by acid catalysis is a reversible reaction. In order to obtain acceptable acetal yields, the equilibrium must be displaced in the direction of acetal synthesis.

Several methods are used to displace the equilibrium towards acetal formation. They number among them the use of a large excess of one of the reactants, in general the alcohol, which then requires elimination of that excess in a step for purification of the desired product. When synthesizing from aldehydes or ketones and alcohols, the best acetal yields are obtained when the water formed is eliminated as the reaction advances. A number of methods can be used to eliminate the water: distillation of an azeotrope between a solvent and water—again, the solvent and water must be at least partially miscible and the boiling points of the different constituents in the reaction medium must be compatible with that azeotrope; or capturing the water by reaction with a chemical compound, for example an ortho-ester or another acetal. However, it should be noted that the secondary products formed in that reaction (for example an ester) render product separation difficult.

The water can also be captured by adsorption on a dehydrating solid which may be calcium sulphate, an aluminum oxide, a copper sulphate, a molecular sieve or any other compound which is known to the skilled person which can capture the water formed without interfering in the reaction which forms the desired product.

The acid catalyst can be soluble in the medium, which is thus homogeneous, however, the soluble catalyst must be neutralized and separated from the other constituents of the reaction medium at the end of the reaction. Thus suitable means must be provided to carry out such treatments.

The use of a soluble catalyst, for example para-toluene sulphonic acid, is not compatible with the use of a molecular sieve to adsorb the water produced, because of interactions between the adsorbent solid and the acid.

WORTEL et al. in "Synthesis of acetals using molecular sieves III, the use of solid acids as catalysts" in Rec. Trav. Chim. Netherlands, 1977, Vol. 96, p. 44–49, describe the use of a solid catalyst with an acidic nature such as a sulphonic resin or a silica-alumina. In the latter case, the catalyst and the dehydrating agent can be regenerated. WORTEL et aL described the use of such a system to synthesize the acetal derived from cyclohexanone and ethanol.

Acetals can generally be synthesized using conventional prior art techniques, and can be synthesized using the transacetalization method but such a synthesis necessitated being able to displace the equilibrium by distilling an alcohol-solvent azeotrope with a suitable boiling point or requires other means which are sometimes difficult to carry out when the solvent does not form an azeotrope with the alcohol used.

In a further aspect, the present invention provides a process for synthesizing acetals with general formula:

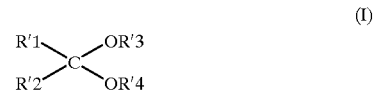

where a non cyclic carbonyl compound such as an aldehyde or a ketone with general formula R'1R'2C=O where R'1 and R1', which may be identical or different, are hydrogen or aryl groups or linear or branched alkyl groups containing 1 to 20 carbon atoms, limits included, reacts with at least one alcohol with general formula R'OH in which R' represents R'3 or R'4 in general formula (I) above and is a linear or branched alkyl group containing 1 to 20 carbon atoms, limits included, preferably 4 to 16 carbon atoms, limits included, characterized in that the synthesis reaction is carried out in a hydrocarbon solvent in the presence of a catalytic composition comprising at least one solid acid catalyst and at least one molecular sieve.

Thus acetals with general formula (I) in which R'3 and R'4 are identical are synthesized from a single alcohol, and acetals with general formula (I) in which R'3 and R'4 are different are synthesized from at least two different alcohols.

In the synthesis process of the invention, the reactants are selected such that the alcohol/carbonyl compound mole ratio is about 1:1 to 10:1; preferably the alcohol/carbonyl mole ratio is about 2:1. The scope of the present invention also encompasses using an excess of carbonyl compound with respect to the stoichiometric conditions, i.e., an alcohol/carbonyl compound mole ratio of about 1:1 to 1:10, limits included.

The advantages of the process of this aspect of the invention includes the possibility of obtaining acetals with good rates of conversion, for example with respect to the alcohol, and at a good reaction rate. The use of a solid catalyst in the process of the invention also has the advantage of enabling this solid catalyst to be isolated easily from the reaction radium. Further, this catalyst is easy to regenerate and after regeneration, its catalytic properties are not altered.

In the particular case of synthesizing 2,2-di(2-ethylhexyloxy)-propane, there is also the possibility of carrying out the synthesis at a reduced cost with respect to conventional transacetalization synthesis from dimethyloxypropane. The synthesis process of the invention applied to 2,2-di(2-ethylhexyloxy)-propane uses a ketone: acetone and an alcohol: 2-ethylhexanoL This synthesis is carried out using reactants which are cheaper than for a synthesis carried out using dimethyloxypropane. The 2,2-di(2-ethylhexyloxy)-propane obtained has the following semi-developed formula:

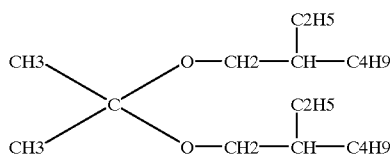

The solid catalytic composition used in the process of the invention is a mixture of a silica-alumina based catalyst and a molecular sieve which will act as an adsorbent for the water produced during the reaction. The reaction equilibrium is thus displaced in the direction of acetal formation. The solid catalytic composition used also has a relatively strong acidic nature which is sufficient to catalyze the reaction. The use of this catalyst can also economize on using a supplemental acid compound.

With respect to the prior art, it should be noted that the acetal obtained is synthesized from a non cyclic ketone, since it is well known to the skilled person that synthesizing acetals from cyclic ketones is easier to carry out than synthesizing acetals from non cyclic acetals. It is thus surprising that acetals can be formed in good yields and with good selectivities from non cyclic ketones using such a solid catalytic composition. Further, the document by WORTEL et al. described above more particularly concerns the synthesis of an acetal which is 1,1-diethoxycyclohexane from a cyclic ketone. WORTEL et al. have studied a number of compositions of mixtures of a molecular sieve with different catalysts for the 1,1-diethoxycyclohexane synthesis reaction, in particular they were interested in a mixture of a molecular sieve with a silica-alumina based catalyst in which the silica-alumina content was 28% by weight.

The acetals of the invention are synthesized from at least one carbonyl compound and at least one alcohol in the presence of a solid catalytic composition containing a molecular sieve and a silica-alumina The silica-alumina used contains about 5% to 95%, preferably 10% to 75%, by weight of alumina. Surprisingly, it has been shown that good yields are obtained when synthesizing acetals from non cyclic ketones using mixture compositions containing about 7% to 20% by weight of silica-alumina, preferably about 10% to 20% by weight and more preferably about 10% to 15% by weight, and about 80% to 93% by weight of molecular sieve. Further, it has been shown that the acetal yield is not increased if a larger amount of silica-alumina is used. The solid catalytic composition obtained after mixing also has the advantage of being capable of being regenerated and of being able to catalyze the reaction at a temperature of the order of room temperature.

The skilled person is aware that a relatively low temperature, for example of about 0° C., encourages the displacement of the reaction equilibrium towards acetal formation. In the synthesis process of the invention, it has been shown that carrying out the reaction at a higher temperature, in particular at a temperature close to room temperature, produces degrees of conversion which are at least as good as those obtained when operating a 0° C. The reaction temperature is about +10° C. to +80° C., preferably about +20° C. to +60° C. and more preferably about +20° C. to +40° C. The reaction can also be carried out between −5° C. and +10° C., however.

Tests have been carried out on a number of types of forms of catalytic composition: powder, extrudates, pellets; and on different arrangements of the constituents of the catalytic composition. This catalytic composition has been tested in the form of extrudates placed in alternating layers of acid catalyst and molecular sieve and in the form of an intimate mixture of powdered acid catalyst and ground molecular sieve. The best conversions were obtained with an intimate mixture of two powders. Without wishing to be bound to any particular theory, it appears logical to assume that the reaction is more easily carried out when the water produced is immediately adsorbed onto the molecular sieve.

The solvent used for the reaction comprises at least one linear or branched alkane or an aromatic compound, these compounds being liquid under the reaction conditions.

This solvent is normally selected from the group formed by hexane, heptane, cyclohexane, toluene, benzene, ethylbenzene and ortho-xylene, used alone or as a mixture. The acetal synthesis reaction is preferably carried out in hexane.

The reaction is carried out under the following operating conditions: a temperature of about −5° C. to +80° C., and an absolute pressure of about 1 to 5 bars. The scope of the invention includes carrying out the reaction under a partial vacuum, for example to about 10 torr (1 torr=133 Pa). Further, care is taken to operate in an atmosphere of dry gas. The term "dry gas" means that this gas contains at most 0.1%, preferably 50 ppm, by weight of water. This gas is normally air, nitrogen or argon, usually dry nitrogen.

The progress of the reaction is followed by regular removal of samples which are analyze using nuclear magnetic resonance (NMR). Thus the conversion of at least one reactant and the yield of the acetal of interest is calculated. When the degree of conversion no longer changes, the reaction is stopped. The desired acetal is then isolated from the other constituents of the reaction medium using suitable separation, washing and purification means to isolate that acetal.

EXAMPLES

Examples 1 to 8 describe the preparation of acetone acetals by transacetalization of 2,2-di(methoxy)-propane using the general procedure described by N. B. Lorette and W. L. Howard in Organic Syntheses Coll. Vol. V, p. 5. We used toluene to eliminate the methanol formed.

The products of Examples 1 to 8 were synthesised as follows.

3 moles of 2,2-di(methoxy)-propane, 6.6 moles of alcohol, 1 liter of toluene and 0.2 g of paratoluenesulphonic acid were introduced into a 3 liter capacity flask.

The flask was connected to a packed fractionation column and the flask contents were distilled at 63° C. until the methanol-toluene azeotrope had been completely eliminated. The residue was then cooled to room temperature then a solution of 0.5 g of sodium methoxide in methanol was added all at once with stirring. The remaining toluene was then eliminated then the alcohol which had not reacted was eliminated by distillation. The desired product was obtained by distillation under reduced pressure.

Example 1

2,2-di-(neopentyloxy)propane or 2,2-di(2,2-dimethylpropanoxy)propane was obtained from an alcohol which was 2,2-dimethylpropanol (6.60 moles).

After distilling the methanol-toluene azeotrope at 63° C. then the toluene and excess 2,2-dimnethylpropanol, the product was obtained by distillation under reduced pressure in the temperature range 60–64° X.

The acetal had the following developed formula:

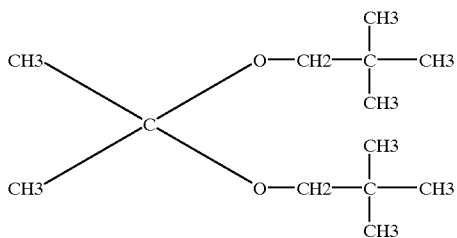

The 2,2-di(neopentyloxy)propane or 2,2-di(2,2-dimethylpropanoxy)propane was characterized by its nuclear magnetic spectrum (NMR):

$^1$H NMR (CD$_2$Cl$_2$) d: 3.05 (s, 4H); 1.31 (s, 6H); 0.90 (s, 18H).

Complexing with Zirconium $5 \times 10^{-3}$ moles of sublimed zirconium chloride was transferred in the absence of moisture to a 100 ml flask under an inert atmosphere, then a hypodermic syringe was used to inject 40 ml of dry, de-aerated toluene. The white suspension was stirred at room temperature using a bar magnet, and $5 \times 10^{-3}$ moles of acetal in solution in 5 ml of toluene were added. The zirconium tetrachloride dissolved in a few minutes to produce a light yellow solution.

Ethylene Oligomerisation Reaction

The following were introduced, in the order given, into a stainless steel autoclave with a working volume of 250 ml provided with a double envelope to regulate the temperature by water circulation, under an argon atmosphere and at room temperature: $2 \times 10^{-3}$ moles of the compound synthesized above, then $1.2 \times 10^{-3}$ moles of ethylaluminium sesquichloride Al$_2$Et$_3$Cl$_3$ in solution in 10 ml of heptane.

The temperature was raised to 95° C. and ethylene was introduced into the autoclave to keep the pressure constant at 6 MPa.

After 2 hours of reaction, ethylene introduction was stopped and the catalyst was destroyed by injecting 2 ml of water under pressure. The activity for oligomerising ethylene to alpha-olefins was calculated from the ethylene consumed; it was 2350 g/g(Zr)/h.

Example 2

2,2-di(hexyloxy)propane was obtained from an alcohol, n-hexanol (6.60 moles).

This acetal had the following semi-developed formula:

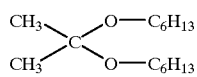

It was isolated by distillation under reduced pressure in the temperature range 58–60° C.

The NMR spectrum exhibited the following displacements:

$^1$H NMR (CD$_2$Cl$_2$) d: 3.36 (t, 4H); 1.4 to 1.6 (m, 18H); 0.85 (t, 6H).

Complexing with Zirconium

This acetal reacted with zirconium tetrachloride using the method described in Example 1 to produce a light orange complex which was soluble in toluene.

The activity of this complex for oligomerizing ethylene to alpha-olefins was determined using the procedure described in Example 1; this activity was 4900 g/g(Zr)/h.

Example 3

2,2-di(decyloxy)propane was obtained from an alcohol, n-decanol (6.60 moles).

This acetal had the following semi-developed formula:

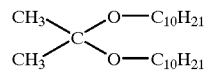

It was obtained by distillation under reduced pressure in the temperature range 80–85° C.

The product was characterized by the following spectra:

IR(NaCl, cm$^{-1}$): 1160 and 1210 (characteristic bands for single C—O bonds);

$^1$H NMR (CD$_2$Cl$_2$) d: 3.36 (t, 4H); 1.4 to 1.6 (m, 4H); 1.2 to 1.4 (m, 34H); 0.88 (t, 6H).

Complexing with Zirconium

This acetal reacted with zirconium tetrachloride using the method described in Example 1 to produce a light yellow complex which was soluble in toluene. The activity of this complex for oligomerising ethylene to alpha-olefins was determined using the procedure described in Example 1; this activity was 3000 g/g(Zr)/h.

Example 4

2,2-di(dodecyloxy)propane was obtained from an alcohol, n-dodecanol (6.60 moles).

This acetal had the following semi-developed formula:

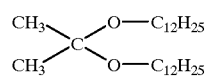

It was obtained by distillation under reduced pressure in the temperature range 85–90° C.; it solidified at room temperature.

The NMR spectrum of this product exhibited the following displacements:

$^1$H NMR (CD$_2$Cl$_2$) d: 3.36 (t, 4H); 1.4 to 1.6 (m, 4H); 1.2 to 1.4 (m, 42H); 0.88 (t, 6H).

Complexing with Zirconium

This acetal reacted with zirconium tetrachloride using the method described in Example 1 to produce a light orange complex which was soluble in toluene and in heptane. The activity of this complex for oligomerizing ethylene to alpha-olefins was determined using the procedure described in Example 1; this activity was 3800 g/g(Zr)/h.

Example 5

2,2-di(tetradecyloxy)propane was obtained from an alcohol, n-tetradecanol (6.60 moles).

This acetal had the following semi-developed formula:

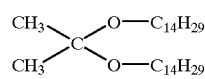

It was isolated by distillation under reduced pressure in the temperature range 125–130° C.; it solidified at room temperature.

The NMR spectrum of this product exhibited the following displacements:

$^1$H NMR (CD$_2$Cl$_2$) d: 3.36 (t, 4H); 1.4 to 1.6 (m, 4H); 1.2 to 1.4 (m, 50H); 0.88 (t, 6H).

Complexing with Zirconium

This acetal reacted with zirconium tetrachloride using the method described in Example 1 to produce a light orange complex which was soluble in toluene and in heptane. The activity of this complex for oligomerizing ethylene to alpha-olefins was determined using the procedure described in Example 1; this activity was 4200 g/g(Zr)/h.

Example 6

2,2-di(hexadecyloxy)propane was obtained from an alcohol, n-hexadecanol (6.60 moles).

This acetal had the following semi-developed formula:

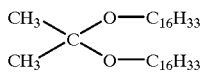

It was obtained by distillation under reduced pressure in the temperature range 130–135° C.; it solidified at room temperature.

The NMR spectrum of this product had the following displacements:

$^1$H NMR (CD$_2$Cl$_2$) d: 3.36 (t, 4H); 1.4 to 1.6 (m, 4H); 1.2 to 1.4 (m, 58H); 0.88 (t, 6H).

Complexing with Zirconium

This acetal reacted with zirconium tetrachloride using the method described in Example 1 to produce a light orange complex which was soluble in toluene and in heptane. The activity of this complex for oligomerising ethylene to alpha-olefins was determined using the procedure described in Example 1; this activity was 3100 g/g(Zr)/h.

Example 7

2,2-di(octadecyloxy)propane was obtained from an alcohol, n-octadecanol (6.60 moles).

This acetal had the following semni-developed formula:

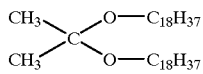

Distillation under reduced pressure produced a first fraction containing octadecanol, and then 2,2-di(octadecyloxy) propane was obtained by more severe distillation and recrystallisation from heptane.

This product could be characterized by the following spectra: IR(KBr, cm$^{-1}$): 1155 and 1208 (characteristic bands for single C—O bonds).

$^1$H NMR (CD$_2$Cl$_2$) d: 3.35 (t, 4H); 1.4 to 1.6 (m, 4H); 1.2 to 1.4 (m, 66H); 0.88 (t, 6H).

Complexing with Zirconium

This acetal reacted with zirconium tetrachloride using the method described in Example 1 to produce a light orange complex which was soluble in toluene and in heptane. The activity of this complex for oligomerizing ethylene to alpha-olefins was determined using the procedure described in Example 1; this activity was 4300 g/g(Zr)/h.

Example 8

2,2-di(tetrahydrofurfuryloxy)propane was obtained from an alcohol, n-tetrahydrofurfuryl alcohol (6.60 moles).

This acetal had the following developed formula:

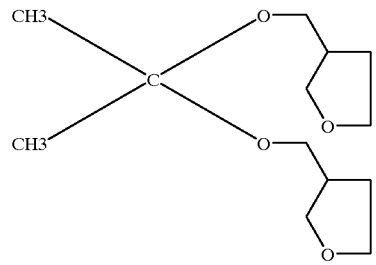

It was isolated by distillation under reduced pressure in the temperature range 83–84° C.

The NMR spectrum of this product had the following displacements:

$^1$H NMR (CD$_2$Cl$_2$) d: 3.6 to 4 (m, 6H); 3.2 to 3.5 (m, 4H); 1.5 to 2 (m, 8H); 1.3 (s, 6H).

Complexing with Zirconium

This acetal reacted with zirconium tetrachloride using the method described in Example 1 to produce an orange complex which remained in suspension in toluene. The activity of this complex for oligomerizing ethylene to alpha-olefins was determined using the procedure described in Example 1; this activity was 960 g/g(Zr)/h.

Example 9

2-methoxy-2-(octadecyloxy)propane was prepared by reacting stearic alcohol (0.025 mole) with 2-methoxypropene (4 equivalents) for 2 hours at 20° C. in the presence of one drop of phosphoryl chloride (POCl$_3$) then adding 5 drops of triethylamine and distilling the excess enol ether.

This acetal had the following semi-developed formula:

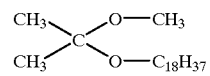

The NMR spectrum of this product had the following chemical displacements:

$^1$H NMR (CD$_2$Cl$_2$) d: 3.34 (t, 2H); 3.14 (s, 3H); 1.4 to 1.6 (m, 2H); 1.1 to 1.4 (m, 36H); 0.88 (t, 3H).

Complexing with Zirconium

This acetal reacted with zirconium tetrachloride using the general procedure described in Example 1 to produce a light orange complex which was soluble in toluene. The activity of this complex for oligomerising ethylene to alpha-olefins was determined using the procedure described in Example 1; this activity was 3500 g/g(Zr)/h.

For Examples 10 to 12, we used the indirect method described by Bal and Pinnick which resulted in very pure products in very good yields.

In this method, a solution of 25×10$^{-3}$ moles of dimethylsulphoxide (Me$_2$SO) in 20 ml of benzene was cooled to 0° C. and 25×10$^{-3}$ moles of trimethylchlorosilane (Me$_3$SiCl) were added.

The mixture was stirred for 10 minutes then 25×10$^{-3}$ moles of alcohol were added.

After heating to reflux overnight, the mixture was cooled, 0.2 g of lithium aluminum hydride (LiAlH$_4$) was added, and refluxing was resumed for 4 hours.

The reaction mixture was then cooled to room temperature and the reaction was stopped by adding water.

The organic phase was washed with water, the aqueous phase was extracted with ether and the combined organic phases were dried with anhydrous magnesium sulphate (MgSO$_4$), filtered then concentrated.

Example 10

2,2-di(hexyloxy)methane was synthesized from n-hexanol. This acetal had the following semi-developed formula:

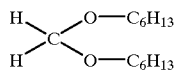

It was isolated by distillation under reduced pressure.

The NMR spectrum of this product had the following displacements:

$^1$H NMR (C$_7$D$_8$) d: 4.6 (s, 2H); 3.45 (t, 4H); 1.4 to 1.7 (m, 4H); 1.1 to 1.4 (m, 12H); 0.85 (t, 6H).

Complexing with Zirconium

This acetal reacted with Zirconium tetrachloride using the method described in Example 1 to produce a colorless complex which was soluble in toluene. The activity of this complex for oligomerizing ethylene to alpha-olefins was determined using the procedure described in Example 1; this activity was 4900 g/g(Zr)/h.

Example 11

2,2-di(2-ethylhexyloxy)methane was synthesized from 2-ethylhexanol. This acetal had the following semi-developed formula:

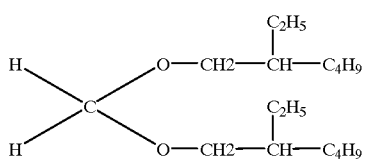

It was isolated by distillation under reduced pressure in the temperature range 104–105° C.

The NMR spectrum of this product had the following chemical displacements:

$^1$H NMR (C$_6$D$_6$) d: 4.64 (s, 2H); 3.46 (d, 4H); 1.2 to 1.7 (m, 18H); 0.92 (t, 12H).

Complexing with Zirconium

This acetal reacted with Zirconium tetrachloride using the method described in Example 1 to produce a colorless complex which was soluble in toluene. The activity of this complex for oligomerizing ethylene to alpha-olefins was determined using the procedure described in Example 1; this activity was 5700 g/g(Zr)/h.

Example 12

2,2-di(hexadecyloxy)methane was synthesized from n-hexanol This acetal had the following semi-developed formula:

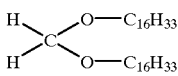

This acetal was prepared using the method described in the two preceding examples. The reaction mixture was filtered over silica, pure 2,2-di(hexadecyloxy)methane was obtained after distilling the octadecanol under reduced pressure, then under a higher vacuum and recrystallising from heptane.

The NMR spectrum of this product had the following displacements:

$^1$H NMR (CD$_2$Cl$_2$) d: 4.6 (s, 2H); 3.48 (t, 4H); 1.4 to 1.7 (m, 4H); 1.1 to 1.4 (m, 52H); 0.88 (t, 6H).

Complexing with Zirconium

This acetal reacted with Zirconium tetrachloride using the method described in Example 1 to produce a colorless complex which was soluble in toluene, heptane and cyclohexane. The activity of this complex for oligomerizing ethylene to alpha-olefins was determined using the procedure described in Example 1; this activity was 5300 g/g(Zr)/h.

Of the synthesised acetals selected to form zirconium complexes for use in forming alpha-olefins by oligomerization, it can be seen that the activity of the complex produced in Example 8, while high, was substantially lower than the activity of complexes formed by the acetals described in the other examples.

The examples below illustrate the final aspect of the present invention without in any way limiting its scope.

In Examples 1' to 6' below, which relate to the second aspect of the present invention, the term "alcohol conversion" is used, i.e., the number of moles of alcohol converted with respect to the ratio of the number of moles of alcohol actually introduced. The term "pure acetal yield" is also used, i.e., the number of moles of acetal recovered after fractionation with respect to the theoretical quantity, one mole of carbonyl compound reacting with 2 moles of alcohol.

Example 1'

(In Accordance with the Invention)

The catalytic composition used to synthesize 2,2-di(2-ethylhexyloxy)propane contained an acid catalyst and a molecular sieve. It was obtained from 280 g of type A molecular sieve sold by Commercial Union under the trade name KA and 46 g of powdered silica-alumina containing 28% by weight of alumina sold by AKZO (KETJEN) under the trade name HAPV. The KA molecular sieve was ground then mixed with the silica-alumina. The catalytic composition obtained was dried at 450° C. in a stream of argon for 10 hours, and had a silica-alumina content of 14% by weight.

This catalytic composition was introduced under dry nitrogen into a reactor with a volume of 2 liters provided with a mechanical stirrer.

In order to synthesize the desired acetal, 1.2 l of dry hexane, 326 g (2.5 moles) of 2-ethylhexanol and 67 g (1.15 moles) of acetone were introduced into the reactor. The mixture was stirred for 5 hours at +25° C., the reaction being carried out at atmospheric pressure in dry nitrogen. The progress of the reaction was monitored by regularly removing samples from the reactor and analysing them by nuclear magnetic resonance (NMR).

The 2-ethylhexanol conversion steadied at 83% by weight with respect to the number of moles of alcohol introduced; this degree of conversion did not change further after 5 hours of reaction.

Stirring was thus stopped, and the solid rapidly settled out. The liquid was extracted, filtered and sent to a flask containing 1 g of sodium methylate. The solid remaining in the reactor was washed with 2×250 ml of hexane.

The liquid fraction was distilled, firstly at atmospheric pressure to recover hexane, then under vacuum to recover pure 2-ethylhexanol (52.8 g), a mixture (15.3 g) of 2-ethylhexanol and acetal (2,2-di-(2-ethylhexyloxy)-propane) then the pure acetal (249.5 g).

The yield of 2,2-di-(2-ethylhexyloxy)propane with respect to the acetone introduced was 72%.

2,2-di-(2-ethylhexyloxy)-propane can be characterized by its infrared spectrum (IR) and by its nuclear magnetic resonance spectrum (NMR).

In infrared spectroscopy, the presence of the characteristic bands of the single C—O bonds of the acetals was noted at 1165 cm$^{-1}$ and 1212 cm$^{-1}$.

The NMR spectrum, recorded in hexadeuterated benzene with formula $C_6D_6$, is shown in the following table:

| Displacement (ppm) | Signal | Number of hydrogen atoms |
|---|---|---|
| 0.85–1.05 | multiplet | 12 |
| 1.2–1.7 | multiplet | 24 |
| 3.39 | doublet (J = 5 Hz) | 4 |

Example 2'
(In Accordance with the Invention)

Under the same conditions as those described for Example 1', 280 g of ground KA sieve was mixed with 31 g of silica-alumina. The silica-alumina content in the catalyst obtained was 10% by weight. The 2-ethylhexanol conversion stabilized at 81.9% by weight with respect to the number of moles of alcohol introduced; this degree of conversion did not change after 5 hours of reaction. The yield of 2,2-di-(2-ethylhexyloxy)propane with respect to the acetone introduced was 71%.

Example 3'

Under the same conditions as those described for Example 1', 280 g of ground KA sieve was mixed with 92 g of silica-alumina. The silica-alumina content in the catalyst obtained was 25% by weight. The 2-ethylhexanol conversion stabilize at 81% by weight with respect to the number of moles of alcohol introduced; this degree of conversion did not change after 5 hours of reaction. The yield of 2,2-di-(2-ethylhexyloxy)propane with respect to the acetone introduced was 69%.

This example 3' shows that, with all other conditions being identical, an amount of 25% by weight of silica-alumina does not lead to a higher conversion of the alcohol introduced.

Example 4'

Comparative

Under the same conditions as those described for Example 1', 140 g of ground KA sieve was mixed with 46 g of silica-alumina. The silica-alumina content in the catalyst obtained was 25% by weight. The 2-ethylhexanol conversion stabilized at 66% by weight with respect to the number of moles of alcohol introduced; this degree of conversion did not change after 5 hours of reaction. The yield of 2,2-di-(2-ethylhexyloxy)propane with respect to the acetone introduced was 60%.

This comparative example shows that, with all other conditions being identical, a smaller amount of molecular sieve, with 25% by weight of silica-alumina leads to a lower conversion of alcohol, and thus there is a minimum quantity of molecular sieve which is necessary to capture the water which is theoretically produced. The term "water which is theoretically produced" means the water produced for complete conversion of the alcohol.

Example 5'
(In Accordance with the Invention)

Under the same conditions as those described for Example 1', 280 g of ground KA sieve was mixed with 46 g of silica-alumina. The silica-alumina content in the catalyst obtained was 14% by weight. The reaction was carried out at 0° C. The 2-ethylhexanol conversion stabilized at 80% by weight with respect to the number of moles of alcohol introduced; this degree of conversion did not change after 5 hours of reaction. The yield of 2,2-di-(2-ethylhexyloxy)propane with respect to the acetone introduced was 70%.

This example shows that, with all other conditions being identical, a lower reaction temperature results in an equivalent alcohol conversion.

Example 6'
(In Accordance with the Invention)

The catalyst used was that used in Example 1 after washing 3 times each with 200 ml of hexane, drying in a stream of air at 450° C. for 10 hours then cooling to room temperature in a stream of dry air.

The 2-ethylhexanol conversion stabilized at 83.7% by weight with respect to the number of moles of alcohol introduced; this degree of conversion did not change after 5 hours of reaction. The yield of 2,2-di-(2-ethylhexyloxy)propane with respect to the acetone introduced was 73%.

It thus appears that the catalytic composition had been regenerated and that the catalytic properties of this composition had not been altered.

What is claimed is:

1. An acetal, wherein the acetal is 2,2-di(tetrahydrofurfuryloxy)propane.
2. A process for producing an acetal according to claim 1, comprising transacetalyzing 2,2-di(methoxy)propane with n-tetrahydrofurfuryl alcohol.
3. A complex of an acetal according to claim 1 with a zirconium compound.
4. A complex according to claim 3 with a zirconium halide.
5. A complex of an acetal according to claim 3 with zirconium tetrachloride.
6. A complex of an acetal according to claim 3, wherein the zirconium compound is an oxycarboxylate derivative or a ZrR'$_4$ derivative where R' is an alkoxy group with formula R"O, or an amido group with formula R"$_2$N or a carboxylate group with formula R"COO, where R" is a hydrocarbyl group or an alkyl group.
7. In a catalytic process for oligomerizing ethylene to alpha-olefins, the improvement wherein the catalyst is a complex according to claim 3.
8. A complex of an acetal according to claim 6, wherein the hydrocarbyl group or the alkyl group of R" contains 1 to 30 carbon atoms.

* * * * *